(12) United States Patent
Wang et al.

(10) Patent No.: US 8,562,848 B2
(45) Date of Patent: Oct. 22, 2013

(54) END POINT DETECTING METHOD OF METAL ETCHING AND DEVICE THEREOF

(75) Inventors: Chin-wen Wang, Shenzhen (CN); Chengming He, Shenzhen (CN)

(73) Assignee: Shenzhen China Star Optoelectronics Technology Co., Ltd., Shenzhen, Guangdong Province (CN)

( * ) Notice: Subject to any disclaimer, the term of this patent is extended or adjusted under 35 U.S.C. 154(b) by 217 days.

(21) Appl. No.: 13/219,700

(22) Filed: Aug. 28, 2011

(65) Prior Publication Data

US 2012/0138572 A1  Jun. 7, 2012

(30) Foreign Application Priority Data

Dec. 2, 2010  (CN) .......................... 2010 1 0575610

(51) Int. Cl.
*B44C 1/22* (2006.01)
*C23F 1/00* (2006.01)
*G01B 11/00* (2006.01)

(52) U.S. Cl.
USPC ....................... 216/85; 216/23; 216/92; 438/8

(58) Field of Classification Search
None
See application file for complete search history.

(56) References Cited

U.S. PATENT DOCUMENTS

| 5,273,935 A | 12/1993 | Morimoto et al. |
| 2003/0087459 A1* | 5/2003 | Laursen et al. ................... 438/8 |
| 2007/0281222 A1 | 12/2007 | Doi et al. |

FOREIGN PATENT DOCUMENTS

| CN | 1898547 A | 1/2007 |
| EP | 0352004 A2 | 1/1990 |
| JP | 58017618 A | 2/1983 |

* cited by examiner

*Primary Examiner* — Anita Alanko
(74) *Attorney, Agent, or Firm* — Cheng-Ju Chiang

(57) ABSTRACT

Disclosed is an end point detecting method of metal etching and a device thereof. The end point detecting method of metal etching comprises: performing scan to a metal film to acquire a proportion of a transparency area of the metal film in a scanned area; judging whether the proportion of the transparency area reaches a predetermined value or not; and confirming a current etching time of the metal film as an etching end point time when the predetermined value is reached. The device comprises an acquirement module, a judgment module and a confirmation module. The acquirement module performs scan to the metal film to acquire the proportion of the transparency area. The judgment module judges whether the proportion reaches the predetermined value or not. The confirmation module confirms the current etching time of the metal film as the etching end point time when the proportion reaches the predetermined value.

10 Claims, 7 Drawing Sheets

END POINT DETECTING METHOD OF METAL ETCHING AND DEVICE THEREOF

BACKGROUND OF THE INVENTION

1. Field of the Invention

The present invention generally relates to an end point detecting method of metal etching and device thereof, and more particularly to an end point detecting method of metal etching and device thereof, capable of eliminating the effect of the set up location for the scanner of the end point detecting device of metal etching and judging the etching end point time of the metal film more precisely.

2. Description of Prior Art

Please refer to FIG. 1, which shows a diagram of that a substrate 100 carrying a metal film is conveyed in a metal wet etching machine 10 when a LCD (Liquid Crystal Display) panel is manufactured. In the LCD panel manufacture, the metal wet etching machine 1 is used for executing a wet etching to the metal film. The metal wet etching is to load the substrate 100 which the surface is plated with the metal film (metal layer) in an etching bath full of acid solution. Then, etching is performed to the area unprotected by the photoresist to obtain the patterns protected by the photoresist. Before the metal wet etching machine 10 is used to perform etching to a batch of metal films. One of the batch of the metal films is selected as being a sample metal film and to acquire an etching end time of the sample metal film. Two ways of performing the etching end time detection exist in the industry nowadays. One is shown in FIG. 2, which shows a diagram of that a work 150 executes a random check for judging the etching end time of the metal films with unaided eye by experience according to prior art. However, this way is less precise because digitized management is unable to realize. The other is to acquire the etching end time of the sample metal film through the scanner 104 of the EPD (End Point Detector). The etching end time is defined as the period of time from loading the substrate 100 into the etching bath full of acid solution till the sensor of the end point detector detects the metal film penetrated by the light (the substrate 100 is used for carrying the metal film).

The working theory of the end point detector is based on the light reflection/penetration. As the metal film remains on the substrate 100, the light generated by the sensor of the end point detector is still reflected by the metal film because the light cannot penetrate the metal film. The end point detector judges that the end point time of the metal film has not arrived hereby; as the metal film carried by the substrate 100 is completely etched, the light generated by the sensor of the end point detector can penetrate the substrate 100 and is not be reflected because the light can penetrate the substrate 100. The end point detector judges that the end point time of the metal film has arrived hereby.

However, as shown in FIG. 3, considering the functions of the metal film on the substrate 100, functioning area 100a and dummy area 100b can be illustrated. The dummy areas 100b are the areas without patterns (without photoresist), and the patterns of the functioning areas 100a are divided into a great many tiny and irregular shaped areas when the exposure process is performed. Therefore, when the functioning areas 100a are etched with acid solution, the etching time is simply related with the thickness of the metal film; but the dummy areas 100b have no patterns and the entire area is relatively larger than the functioning areas 100a, when the dummy areas 100b are etched with acid solution, the etching happens from the exterior to the interior slower. The dummy areas 100b have the same thickness as the functioning areas 100a do but the needed etching time takes longer.

Although, the etching end time of each metal film can be detected with the way through the end point detector, the set up location for the scanner 104 affects the judgment of end point time directly because the end point detector according to prior art as shown in FIG. 4 utilizes a single point scanning manner. Generally, the set up location of the scanner 104 is a fixed position as performing scan. However, the distributions of the functioning areas 100a and the dummy areas 100b are different in the metal films of different substrates. If the fixed position of the scanner 104 makes the scan covers the dummy areas 100b most, it results in that the detected end point time can be longer than the really needed etching point time. Then, the error of the judgment of the end point time obviously becomes larger.

Consequently, there is a need to provide an end point detecting method of metal etching and device thereof for solving the existing drawbacks of aforementioned prior art.

SUMMARY OF THE INVENTION

An objective of the present invention is to provide an end point detecting method of metal etching and device thereof, capable of eliminating the effect of the set up location for the scanner of the end point detecting device of metal etching and judging the etching end point time of the metal film more precisely.

For realizing the aforesaid objective of the present invention, the present invention provides an end point detecting method of metal etching, utilized with an end point detecting device of metal etching. The end point detecting method of metal etching of the present invention comprises steps below: performing scan to a metal film with a scanner to acquire a proportion of a transparency area of the metal film in a scanned area; judging whether the proportion of the transparency area of the metal film in the scanned area reaches a predetermined value or not, and if the predetermined value is not reached, then executing the step of performing scan to the metal film again after a preset latency; confirming a current etching time of the metal film as an etching end point time when the predetermined value is reached, wherein the length of the scanner is larger than or equal to the width of a substrate carrying the metal film.

In one embodiment of end point detecting method of metal etching of the present invention, the end point detecting device comprises a scanner to perform scan to the metal film, and the scanner is positioned with the direction of the length perpendicular to a conveying direction of a substrate carrying the metal film to make the scanned area obtained by the scanner cross the width of the substrate.

In one embodiment of end point detecting method of metal etching of the present invention, the area of the scanner is equal to the area of the substrate carrying the metal film.

In one embodiment of end point detecting method of metal etching of the present invention, the predetermined value of the proportion is 50%-75%.

For realizing the aforesaid objective of the present invention, the present invention provides an end point detecting method of metal etching, comprising: an acquirement module, performing scan to a metal film to acquire a proportion of a transparency area of the metal film in a scanned area; a judgment module, judging whether the proportion of the transparency area of the metal film in the scanned area reaches a predetermined value or not; and a confirmation module, confirming a current etching time of the metal film as an etching end point time when the judgment module judges that the proportion of the transparency area of the metal film in the scanned area reaches the predetermined value.

In one embodiment of end point detecting method of metal etching of the present invention, if the judgment module judges that the proportion of the transparency area of the metal film in the scanned area does not reach the predetermined value, the acquirement module is triggered to perform scan to the metal film.

In one embodiment of end point detecting method of metal etching of the present invention, the acquirement module further comprises: a scanner, performing scan to the metal film to obtain the transparency area of the metal film; and a proportion acquiring unit, acquiring the proportion of the transparency area of the metal film in the scanned area.

In one embodiment of end point detecting method of metal etching of the present invention, the length of the scanner is larger than or equal to the width of a substrate carrying the metal film to make the scanned area obtained by the scanner cross the width of the substrate.

In one embodiment of end point detecting method of metal etching of the present invention, the predetermined value of the proportion is 50%-75%.

According to the end point detecting method of metal etching and the device thereof, the effect of the set up location for the scanner of the end point detecting device of metal etching can be eliminated to judging the etching end point time of the metal film more precisely, accordingly, to promote the yield of the LCD panel manufacture.

DETAILED DESCRIPTION OF THE INVENTION

Detail descriptions of the specific embodiments of the adjustment method of the LCD overdrive voltage and the device thereof provided by the present invention in conjunction with the attached figures are introduced below.

Figure 1:
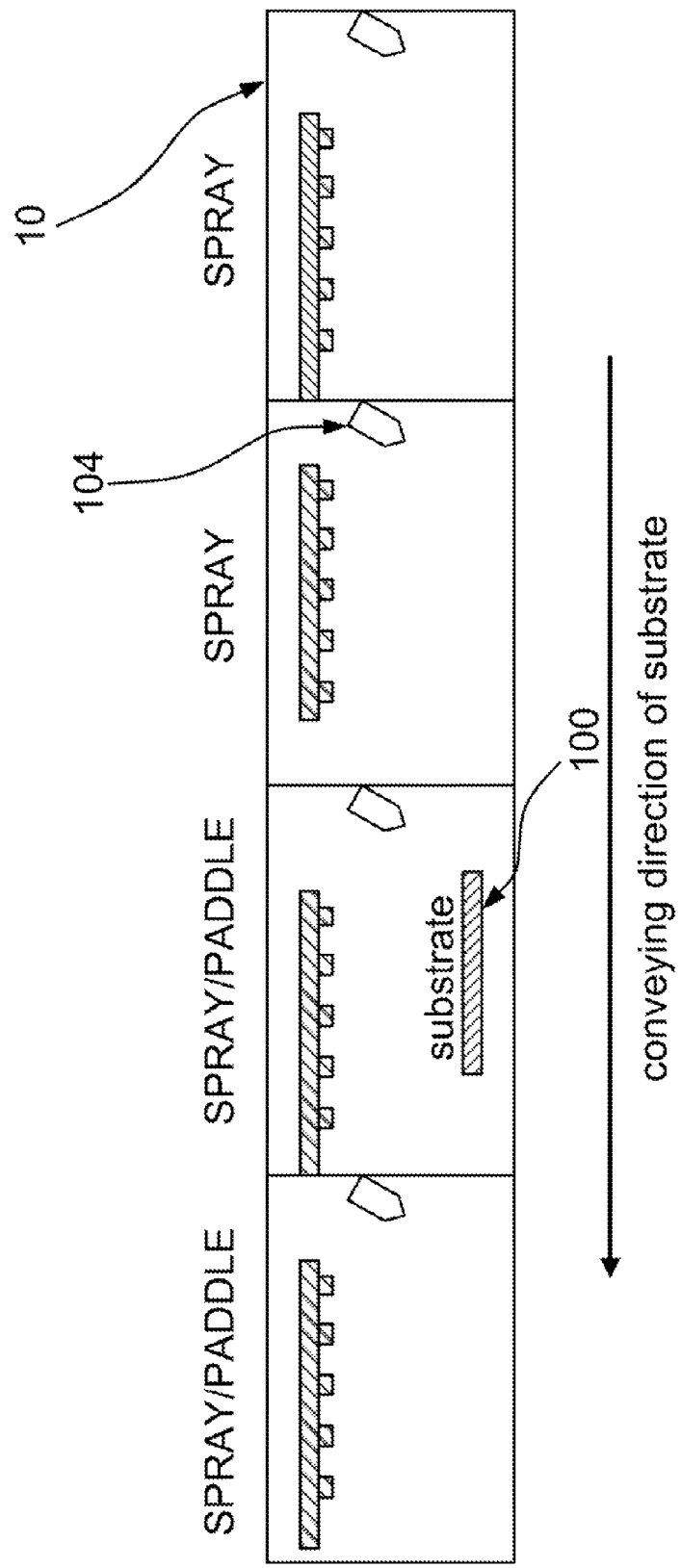
FIG. 1 shows a diagram of that a substrate carrying a metal film is conveyed in a metal wet etching machine when a LCD panel is manufactured.
Figure 2:
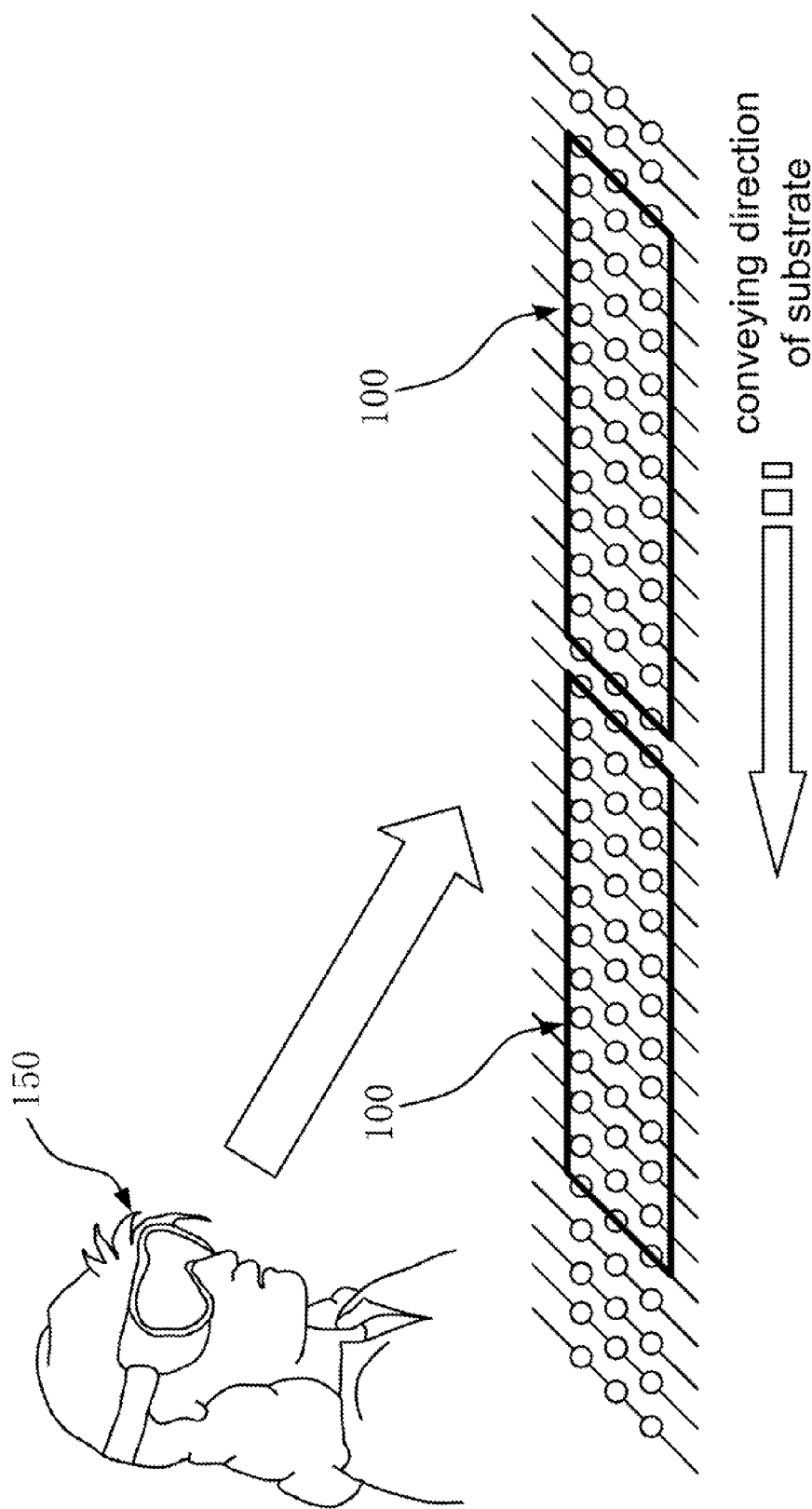
FIG. 2 shows a diagram of that a work executes a random check for judging the etching end time of the metal films with unaided eye according to prior art.
Figure 3:
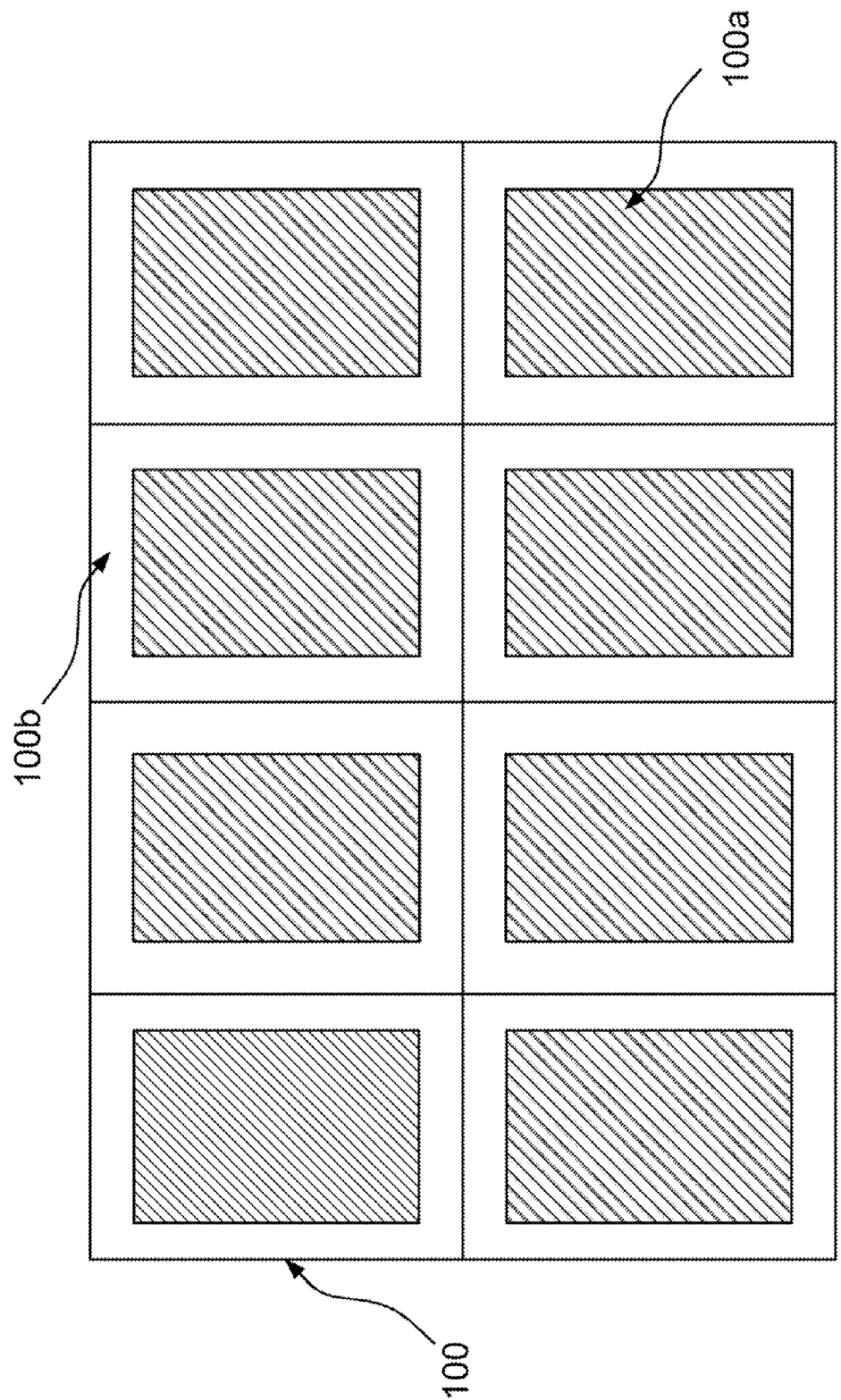
FIG. 3 shows a diagram of the metal film carried by the substrate of the LCD panel which has functioning areas and dummy areas.
Figure 4:
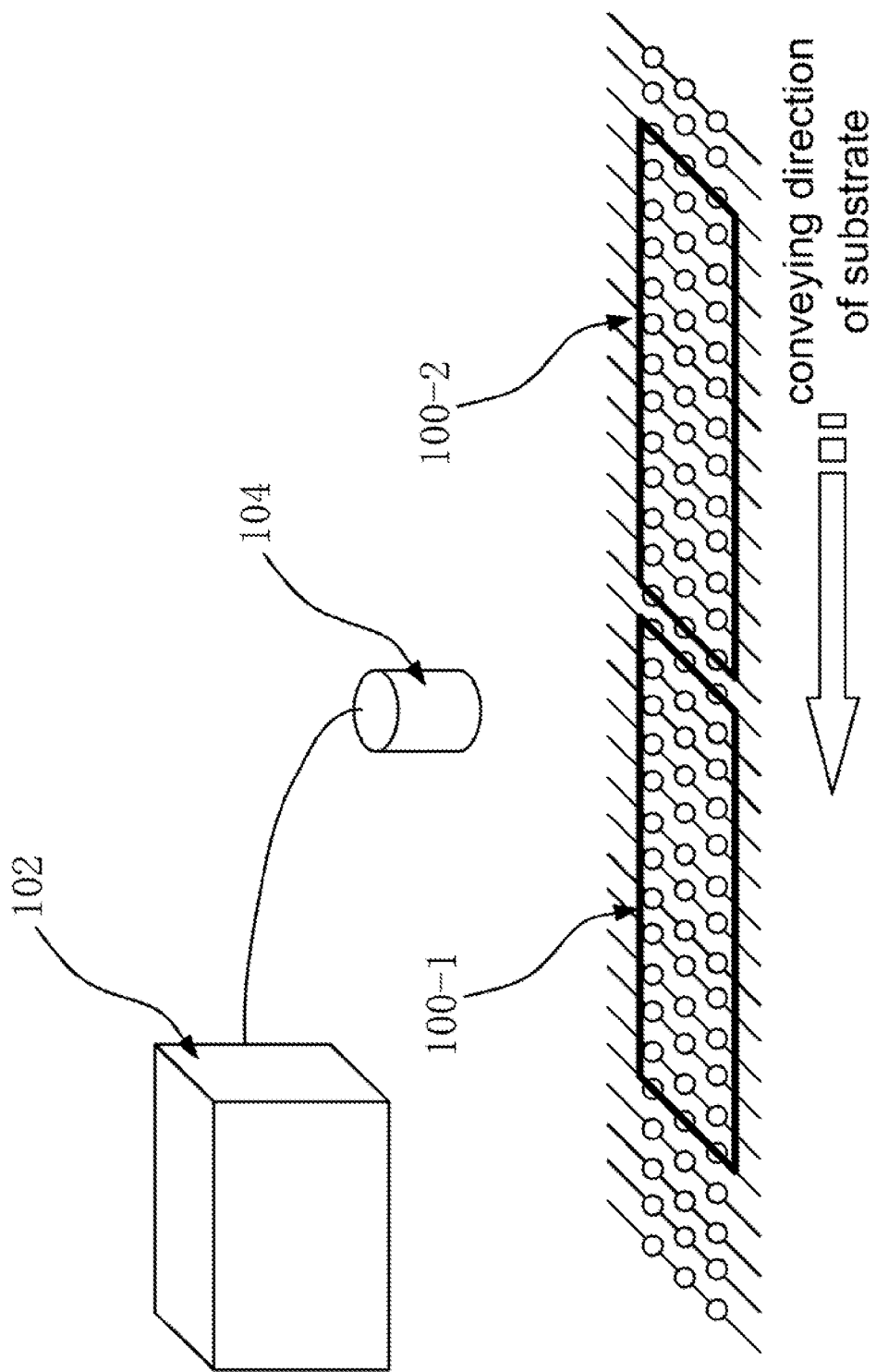
FIG. 4 shows a diagram of that an end point detecting device of metal etching according to prior art is utilized for judging the etching end time of the metal film.
Figure 5:
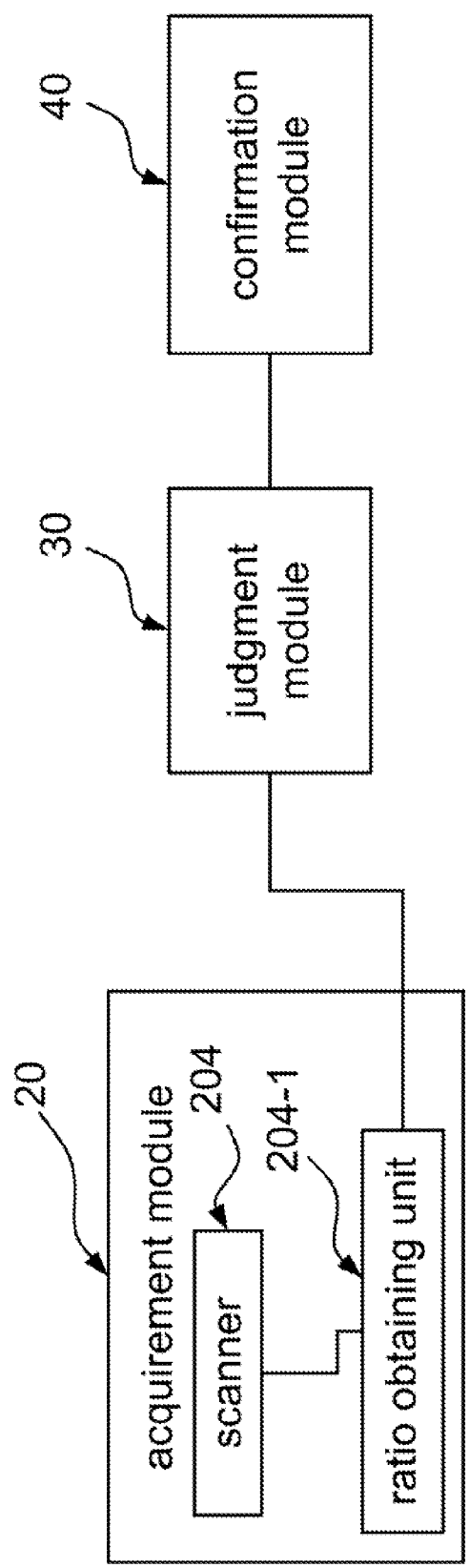
FIG. 5 shows a block diagram of an end point detecting device of metal etching according to the present invention.
Figure 6:
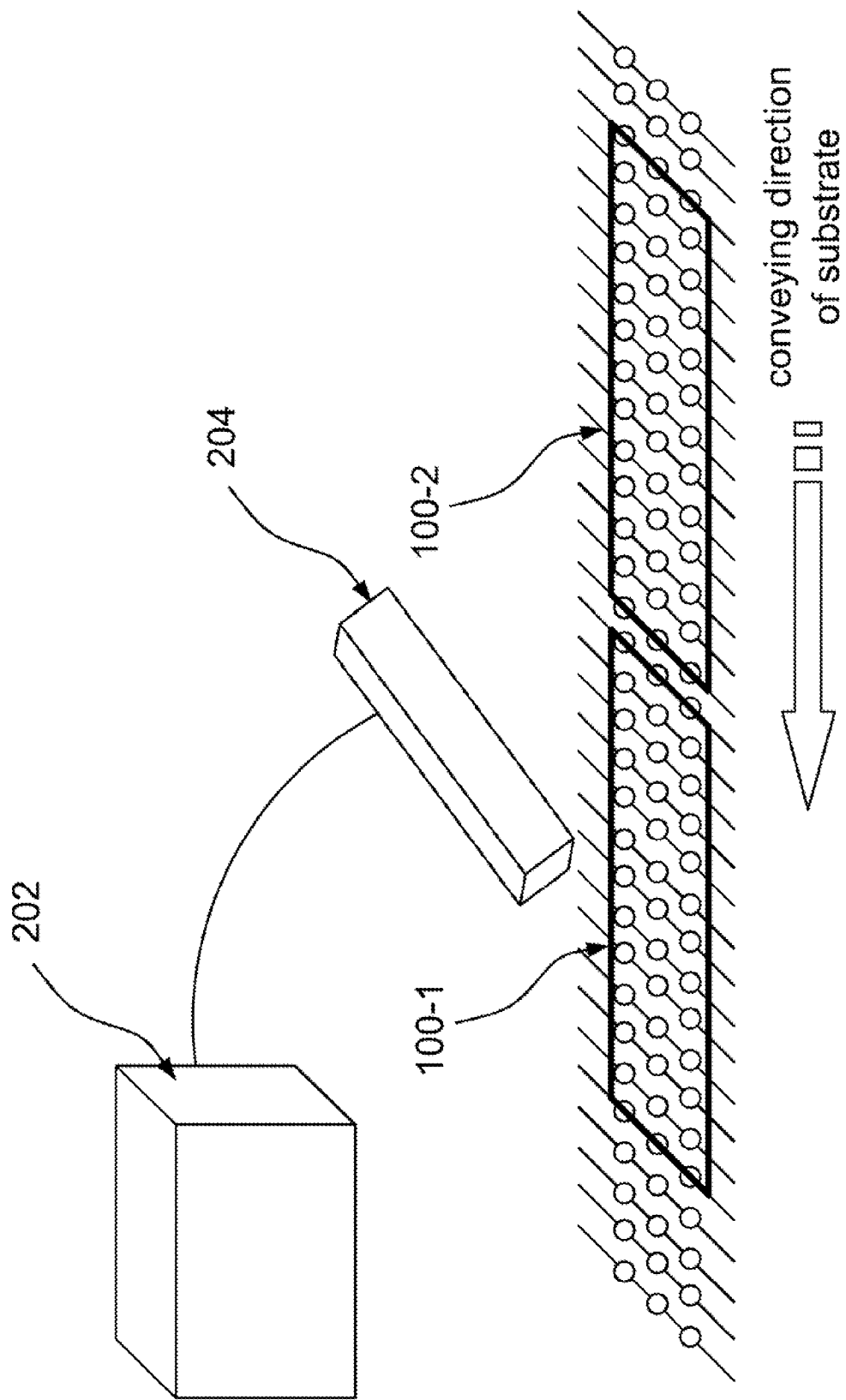
FIG. 6 shows a diagram of that an end point detecting device of metal etching according to the present invention is utilized for judging the etching end time of the metal film.
Figure 7:
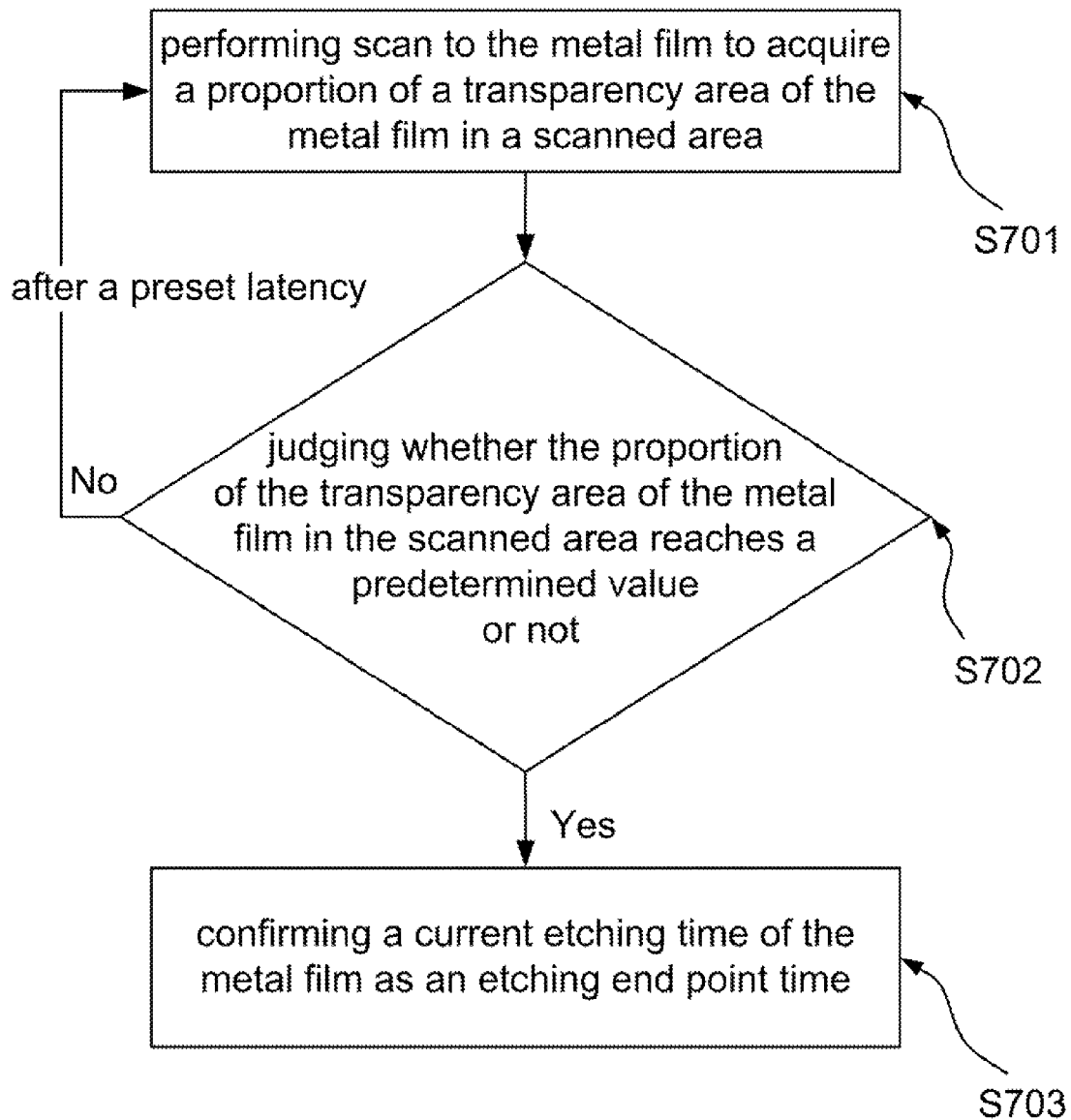
FIG. 7 shows a flowchart of an end point detecting method of metal etching according to the present invention.

Please refer to FIG. 3, FIG. 5, FIG. 6 and FIG. 7. FIG. 5 shows a block diagram of an end point detecting device of metal etching according to the present invention. FIG. 6 shows a diagram of that an end point detecting device of metal etching according to the present invention is utilized for judging the etching end time of the metal film. FIG. 7 shows a flowchart of an end point detecting method of metal etching according to the present invention. As shown in FIG. 5, the end point detecting device of the present invention comprises an acquirement module 20, a judgment module 30 and a confirmation module 40. The acquirement module is utilized to perform scan to a metal film to acquire a proportion of a transparency area of the metal film in a scanned area; the judgment module 30 is utilized to judge whether the proportion of the transparency area of the metal film in the scanned area reaches a predetermined value or not; and the confirmation module 40 is utilized to confirm a current etching time of the metal film as an etching end point time when the predetermined value is reached.

As shown in FIG. 6, in this embodiment of the present invention, the end point detecting controller 202 can be a specific embodiment of the judgment module 30 and the confirmation module 40 but not limited thereto. The acquirement module 20 can comprise the scanner 204 and the proportion acquiring unit 204-1 shown in FIG. 5 as being the specific embodiment but not limited thereto.

In this embodiment of the present invention, the scanner 204 is utilized to perform scan to the metal film to obtain the transparency area of the metal film. The proportion acquiring unit 204-1 is utilized to acquire the proportion of the transparency area of the metal film in the scanned area. The scanner 204 can be optical scanner as illustration and the spectrum range and the specification can be determined according to the material of the metal film. The proportion acquiring unit 204-1 can be an ASIC as illustration; or the scanner 204, the judgment module 30 and the confirmation module 40 are combined as an integral detection apparatus; alternatively, the portion of the proportion acquiring unit 204-1, the judgment module 30 and the confirmation module 40 can be realized by hardware circuits or respective functions thereof can be realized by software programs but not limited thereto.

Furthermore, the scanner 204 in the acquirement module 20 of the end point detecting device of metal etching according to the present invention can be an individual detecting element. The proportion acquiring unit 204-1, the judgment module 30 and the confirmation module 40 can be specifically realized by the interior control mechanism of the metal wet etching machine. Alternatively, all of the acquirement module 20, the judgment module 30 and the confirmation module 40 in the present invention can be specifically realized by the interior control mechanism of the metal wet etching machine.

In this embodiment of the present invention, the scanner 204 can be located inside the metal wet etching machine to perform scan to the metal films carried by the substrates 100-1 or 100-2. The working theory of the scanner 204 is introduced below: the light generated by the scanner 204 is emitted onto the metal films of the substrates 100-1 or 100-2 to perform scan to the metal films. Meanwhile, the scanner 204 further comprises a receptor (not shown) to detect whether the emitted light is reflected by the metal films of the substrates 100-1 or 100-2. The scanner 204 obtains the reflection values by the receptor and transforms the reflection values into signals to be acquired by the proportion acquiring unit 204-1 via a DAC.

After that, the end point detecting controller 202 receives the signals from the proportion acquiring unit 204-1 to judge whether the proportion of the transparency area of the metal film in the scanned area reaches a predetermined value or not. The end point detecting controller 202 in this embodiment can calculate the proportion of the transparency area of the metal film of the substrates 100-1 or 100-2 in the scanned area in real time. When the predetermined value is reached, the current etching time of the metal film can be confirmed as an etching end point time. In another word, the period of time from loading the substrate with metal film into the metal wet etching machine till the current etching time is the end point time. According to the experiment results of the inventors, the predetermined value of the proportion is preferably 50%~75%.

Furthermore, as shown in FIG. 6, in this embodiment of the present invention, the scanner 204 can have a rod-like appearance. The scanner 204 can be positioned with the direction of the length perpendicular to a conveying direction of the substrates 100-1 or 100-2 carrying the metal film. Namely, the scanner 204 is transversely positioned relative to the conveying direction of the substrates 100-1 or 100-2 in the metal wet etching machine. Moreover, the length of the scanner 204 can be larger than or equal to the width of the substrate. Thus, the scanned area obtained by the scanner 204 can cross the width of the substrate 100-1 or 100-2 for completely scanning the metal film thickness of the substrate 100-1 or 100-2. Therefore, either of the functioning area 100*a* or the dummy area 100*b* shown in FIG. 3 can be covered within the scanned area obtained by the scanner 204. That is, the scanning area of the scanner 204 can cover the entire area of the metal film and perform scan to confirm the etched status of the entire metal film area in real time. Because the scanned area obtained by the scanner 204 covers the functioning area 100*a* and the dummy area 100*b* of the metal film, unlike prior art, because the scanned area of the scanner 104 according to covers the dummy areas 100*b* more, the more obvious error to the judgment of the of end point time happens when the judgment of the end point time is performed.

In the embodiment of the present invention, as considering the 7.5 generation LCD panel manufacture, the optimal cut size of the substrate is 2250 mm×1950 mm. Therefore, the length of the scanner 204 is preferably larger than 1950 mm; as considering the 8.5 generation LCD panel manufacture, the optimal cut size of the substrate is 2500 mm×2200 mm. Therefore, the length of the scanner 204 is preferably larger than 2200 mm. Meanwhile, if the inner space is enough and the conditions are possible, the area of the scanner 204 even can be equal to the entire substrate. Then, the scanner 204 can be set up over the substrate but not limited thereto. As long as the real performed scan can allow the etched status of the metal film to be confirmed.

Please refer to FIG. 6 and FIG. 7. The end point detecting method of metal etching of the present invention can be utilized with the end point detecting device shown in FIG. 6 comprising the end point detecting controller 202 and the scanner 204 to precisely judge the end point time for each of metal films.

In the embodiment of the present invention, the end point detecting method of metal etching of the present invention comprises steps below:

Step 701: performing scan to the metal film to acquire a proportion of a transparency area of the metal film in a scanned area;

Step 702: judging whether the proportion of the transparency area of the metal film in the scanned area reaches a predetermined value or not, and if the predetermined value is not reached, then returning to Step 701 to executing the step of performing scan to the metal film again after a preset latency, and if the proportion of the transparency area reaches the predetermined value, then proceeding the next step, Step 703; and Step 703: confirming a current etching time of the metal film as an etching end point time.

In conclusion, the present invention is capable of eliminating the effect of the set up location for the scanner of the end point detecting device of metal etching and judging the etching end point time of the metal film more precisely. Accordingly, the yield of the LCD panel manufacture can be improved further.

As is understood by a person skilled in the art, the foregoing preferred embodiments of the present invention are illustrative rather than limiting of the present invention. It is intended that they cover various modifications and similar arrangements be included within the spirit and scope of the appended claims, the scope of which should be accorded the broadest interpretation so as to encompass all such modifications and similar structure.

What is claimed is:

1. An end point detecting method of metal etching, utilized with an end point detecting device of metal etching having a scanner, comprising steps of:
   performing scan to a metal film with a scanner to acquire a proportion of a transparency area of the metal film in a scanned area;
   judging whether the proportion of the transparency area of the metal film in the scanned area reaches a predetermined value or not, and if the predetermined value is not reached, then executing the step of performing scan to the metal film again after a preset latency; and
   confirming a current etching time of the metal film as an etching end point time when the predetermined value is reached;
   wherein the length of the scanner is larger than or equal to the width of a substrate carrying the metal film.

2. The end point detecting method of metal etching of claim 1, wherein the scanner is positioned with the direction of the length perpendicular to a conveying direction of the substrate to make the scanned area obtained by the scanner cross the width of the substrate.

3. The end point detecting method of metal etching of claim 1, wherein the area of the scanner is equal to the area of the substrate carrying the metal film.

4. The end point detecting method of metal etching of claim 1, wherein the predetermined value of the proportion is 50%~75%.

5. An end point detecting method of metal etching, utilized with an end point detecting device of metal etching, comprising steps of:
   performing scan to a metal film to acquire a proportion of a transparency area of the metal film in a scanned area;
   judging whether the proportion of the transparency area of the metal film in the scanned area reaches a predetermined value or not; and
   confirming a current etching time of the metal film as an etching end point time when the predetermined value is reached.

6. The end point detecting method of metal etching of claim 5, wherein if the predetermined value is not reached in the step of judging the proportion of the transparency area of the metal film in the scanned area, then executing the step of performing scan to the metal film again.

7. The end point detecting method of metal etching of claim 5, wherein the end point detecting device of metal etching further comprises a scanner to perform scan to the metal film, and the scanner is positioned with the direction of the length perpendicular to a conveying direction of a substrate carrying the metal film.

8. The end point detecting method of metal etching of claim 5, wherein the end point detecting device of metal etching further comprises a scanner, and the length of the scanner is larger than or equal to the width of a substrate carrying the metal film to make the scanned area obtained by the scanner cross the width of the substrate.

9. The end point detecting method of metal etching of claim 5, wherein the end point detecting device of metal etching further comprises a scanner, and the area of the scanner is equal to the area of the substrate carrying the metal film.

10. The end point detecting method of metal etching of claim 5, wherein the predetermined value of the proportion is 50%~75%.

* * * * *